United States Patent [19]

Brace

[11] Patent Number: 5,381,228
[45] Date of Patent: Jan. 10, 1995

[54] RAPID ESTIMATION OF THE OXYGEN PERMEATION RATE OF A THIN FILM ON A PLASTIC CONTAINER

[75] Inventor: John G. Brace, Brown Deer, Wis.

[73] Assignee: Hoover Universal, Inc., Plymouth, Mich.

[21] Appl. No.: 129,509

[22] Filed: Sep. 30, 1993

[51] Int. Cl.$^6$ ............................ G01B 11/06; G01J 3/00
[52] U.S. Cl. ................................... 356/300; 356/382; 250/339.11; 250/341.1
[58] Field of Search ................... 250/339, 341; 356/51, 356/300, 381, 382

[56] References Cited

U.S. PATENT DOCUMENTS 5,015,856  5/1991  Gold .

OTHER PUBLICATIONS

David H. Haaland and Edward V. Thomas; Partial Least-Squares Methods for Spectral Analysis, parts 1 and 2; Analytical Chemistry, vol. 60, 1988; pp. 1193-1208.

David M. Haaland; Quantitative Infrared Analysis of Borophosphosiliicate Films Using Multivariate Statistical methods; Analytical Chemistry, vol. 60, 1988; pp. 1208-1217.

Software manual for "PLSplus" software, version 2.2, published by Galactic Industries Corporation, Salem, N.H. Dated Aug. 1, 1991.

Primary Examiner—F. L. Evans
Assistant Examiner—Peter J. Rashid
Attorney, Agent, or Firm—Leonard J. Kalinowski; E. L. Levine; Joseph E. Root, III

[57] ABSTRACT

A method and apparatus are disclosed for the rapid estimation the macroscopic physical properties of a coating applied to an article such as, for example, a container for food, beverages, or the like. The invention is usable with macroscopic physical properties including permeation rate, thickness of the coating, and others. According to the invention, a prediction model is prepared based on correlations between an infrared absorption spectrum and corresponding measured values of the macroscopic physical property. Thenceforth, the macroscopic physical property does not need to be measured directly, but rather is estimated based on the prediction model with a measured infrared absorption spectrum as an input thereto. A significant savings of time may thereby be realized, since the infrared absorption spectrum is more easily and quickly obtained than direct, actual measurement of many macroscopic physical properties of interest. The rapid and accurate measurement of permeation rate utilizing spectroscopic analysis is a principal application of the invention.

11 Claims, 4 Drawing Sheets

RAPID ESTIMATION OF THE OXYGEN PERMEATION RATE OF A THIN FILM ON A PLASTIC CONTAINER

BACKGROUND OF THE INVENTION

The present invention relates generally to the field of test apparatus, and more particularly to the field of test apparatus for thin film coatings applied to the surface of articles.

Articles formed of plastic materials are often coated with a thin film coating in order to enhance certain properties of the resulting article. In particular, plastic articles are often used as containers for food, beverages, or the like, but such containers are generally found to be lacking in certain physical properties. Thin film coatings are therefore used to enhance the physical properties of the containers. One of the most common purposes for such coatings is to form a barrier against permeation of gasses through the container walls. For example, reduction of the oxygen permeation rate helps to retard spoilage of a foodstuff in the container, while reduction of the carbon dioxide permeation rate helps to maintain a high level of carbonation in carbonated beverages. One common coating which is widely used is an $SiO_2$ coating, which forms a very thin, glass-like layer having very good barrier properties.

A major difficulty with volume production of such coated containers is that periodic sampling of production containers is required to ensure that the coating is performing to the desired specifications. In the prior art, the periodic sampling required actual, direct measurement of the physical property of interest. Some of the required measurements, however, are extremely painstaking and time consuming to perform. In the case of permeation rate, for example, the actual, direct measurement thereof requires a substantial amount of large test equipment and apparatus, including gas supply, plumbing, an environmental enclosure, precision gas detectors, etc. In addition, the permeation rates of the coated containers are so low that a test cycle usually lasts for several weeks, and typically spans eight weeks, before a steady state permeation condition can be achieved and accurately measured.

Accordingly, a need exists for a faster, simpler method for measuring the macroscopic physical properties of a thin film coating, e.g. those properties which are macroscopically observable and/or measurable. That goal is achieved in the present invention.

SUMMARY OF THE INVENTION

The broad goal of the present invention is to provide a method for rapidly and accurately measuring the oxygen permeation rate of a thin film coating applied onto a container for consumable food products.

Another object of the invention is to utilize spectroscopic analysis to firstly prepare a prediction model for estimating oxygen permeation rate based on an input spectral component value corresponding to absorption of electromagnetic radiation in at least one frequency band of the radiation, and secondly evaluate the prediction model based on a measured absorption spectrum for an unknown thin film coating to provide an accurate, estimated value as a measurement of the oxygen permeation rate exhibited by the unknown thin film coating. Thus, the invention permits measurement of the oxygen permeation rate for thin film coatings which in the prior art have been very complicated and time consuming to measure directly, by the greatly simplified measurement of an absorption spectrum.

Yet another object of the invention is to provide automated measurements of the oxygen permeation rate for thin film coatings. Because of the greatly simplified measurement of an absorption spectrum, the invention provides a capability for automated, production line measurement of oxygen permeation rate for thin film coatings which heretofore had required weeks of laboratory testing.

These and other objects are achieved in the present invention of a method and apparatus for measuring oxygen permeation rate for thin film coating. The method according to the invention includes the following steps. The first step is preparing a prediction model. The prediction model accepts as an input at least one spectral component value corresponding to absorption of electromagnetic radiation in at least one frequency band of the radiation. This is often referred to as an "absorption spectrum" for the thin film coating. The prediction model may be an equation, or formula, which translates the input absorption spectrum into an output value, which is an estimated measurement for a corresponding oxygen permeation rate. After preparing the prediction model, the second step is performing spectroscopic analysis of the unknown thin film coating to obtain at least one sample spectral component value corresponding to the absorption of electromagnetic radiation in said at least one frequency band by the unknown thin film coating, e.g. the "absorption spectrum" corresponding to the unknown thin film coating. Thirdly, the prediction model is evaluated with the "absorption spectrum" corresponding to the unknown thin film coating as the input. The output of the prediction model is then a measurement of the oxygen permeation rate exhibited by the unknown thin film coating.

The invention is especially advantageous when utilized in conjunction with thin film coatings applied to plastic containers for consumable food products. Thin film barrier coatings have been found to be effective for reducing the permeation of gasses with small molecular size, such as oxygen, which could otherwise lead to premature spoilage of the food product within the container. The invention provides a needed quality control and measurement tool to facilitate the use of thin film coatings on food product containers.

In the method according to the invention, the step for preparing the prediction model may include correlating an absorption spectrum obtained from a thin film analysis coating with an actual, direct measurement of oxygen permeation rate of a thin film control coating. The analysis coating and the control coating are both applied using the same, or approximately the same, process conditions, so that both respective coatings have approximately the same physical characteristics. The correlation may then be subjected to multivariate regression analysis to produce the prediction model.

In another preferred embodiment of the invention, a selected subset of the correlations may be used in the multivariate regression analysis. Specifically, those correlations which most strongly correlate specific spectral components of the absorption spectrum to the actual, direct measurement of the oxygen permeation rate may be selected for participation in the multivariate regression analysis, and the resulting prediction model thus achieves an even greater accuracy.

Other embodiments of the invention may employ any spectroscopy mode, including, but not limited to, normal incidence transmission mode, attenuated total reflection mode, and external reflection mode. The invention may further employ witness sample collected to facilitate the spectroscopy of the thin film coatings. The witness sample collectors may be applied prior to application the thin film coating, whereby after the coating is completed, the witness sample collectors may be removed and analyzed in a normal incidence transmission mode spectrometer to obtain spectral components corresponding to the coating/witness sample collector combination. The use of witness sample collectors permits an absorption spectrum to be obtained which corresponds only to the coating, and not the underlying structure, by unity subtraction of spectral components corresponding to the absorption characteristics of the witness sample collector itself from the spectral components corresponding to the coating/witness sample collector combination.

An apparatus according to the invention is also contemplated for carrying out the aforementioned method.

DETAILED DESCRIPTION OF PREFERRED EMBODIMENTS

This invention deals with methods and apparatus for measuring physical properties of thin film coatings, particularly thin film coatings applied to containers for consumable food products and the like. The invention applies to measurement of any of several possible macroscopic physical properties, but the macroscopic physical property generally involved in the preferred embodiment is the property of oxygen permeation rate. Overall, the invention utilizes a spectroscopic analysis of a thin film coating to allow an accurate prediction of the macroscopic physical properties of the coating. The spectroscopic analysis can be performed relatively rapidly, and is amenable to automated testing.

Figure 1:
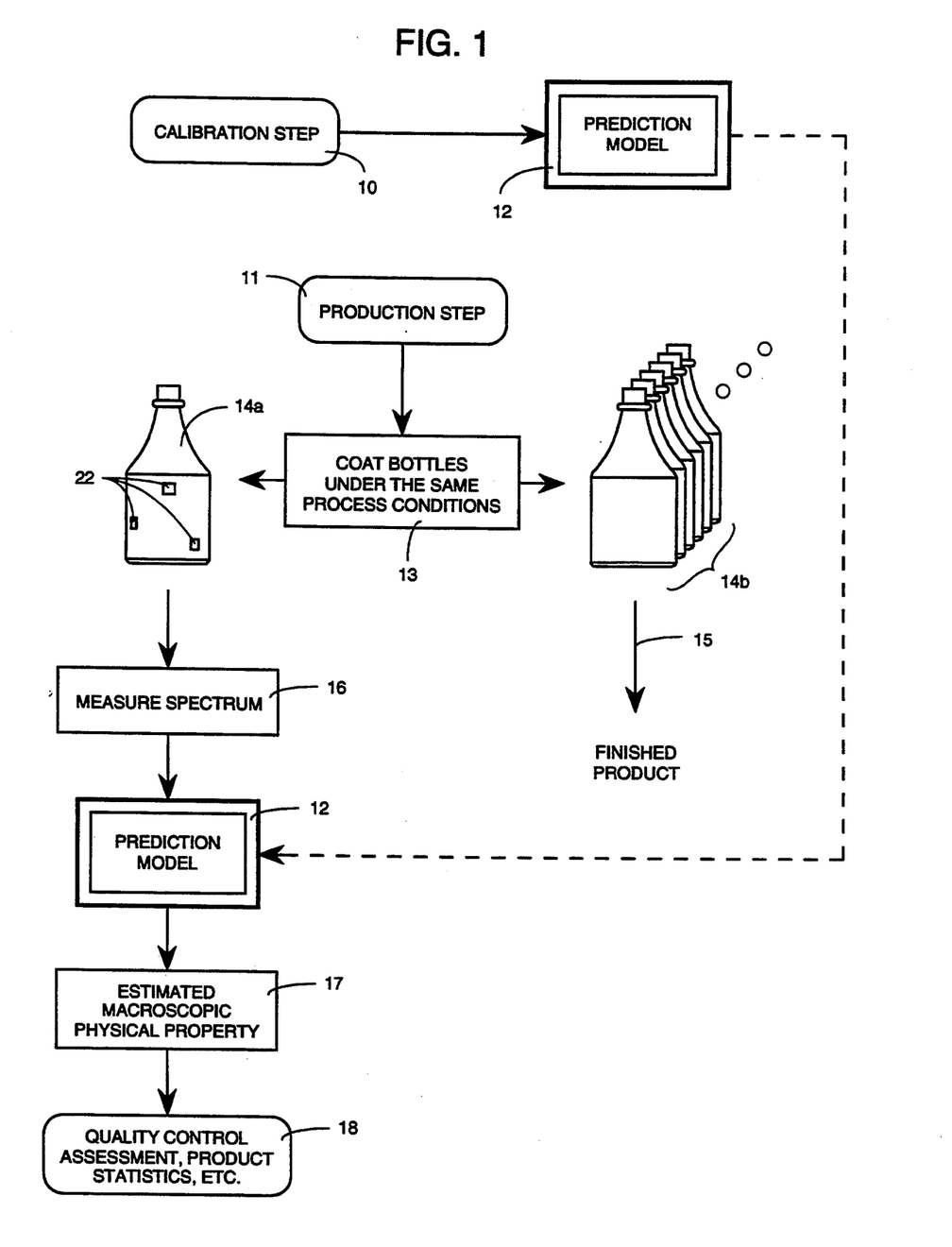
FIG. 1 is a schematic diagram of the method and apparatus of the invention.

An overall measurement apparatus and method according to the present invention is represented schematically in FIG. 1. Generally, the invention involves two separate steps; a calibration step 10 and a production step 11. In the calibration step 10, a prediction model 12 is prepared based on both (a) a spectroscopic analysis of a given coating, and (b) measurement of at least one macroscopic physical property of that same, or a similar, coating. The prediction model 12 prepared in the calibration step 10 is then later used in the production step 12 for estimation of the macroscopic physical property without the necessity for performing an actual physical measurement of the same.

The measurement of the macroscopic physical property in the calibration step 10 is an actual direct measurement of a particular macroscopic characteristic, e.g. an observable, measurable quantity such as, for example, any one of the following:

(a) the thickness of the coating;

(b) the permeation rate of the coating with respect to specific gasses, i.e. oxygen or carbon dioxide;

(c) chemical etch rate or other reactivities; or (d) percent extractables, e.g. for use in food contact.

The foregoing list is only illustrative of the types of physical properties for which the invention may be applied, and is not an exclusive list thereof. The invention therefore has wide application to a number of different properties, which are herein referred to in general as macroscopic physical properties. Although the invention is applicable to many different macroscopic physical properties, a greater benefit is realized when applying the invention to those macroscopic physical properties which are most difficult to measure directly. For example, a direct measurement of permeation rate may take up to several weeks, as noted above. One advantage of this invention, however, is that once the prediction model 12 is established by the calibration step 10, no further direct measurements of the macroscopic physical property are needed. The subsequent production step 11 utilizes spectroscopic measurements which can be obtained quickly (e.g. in a few minutes or less) in conjunction with the prediction model 12 to estimate what the response of the coating would be in regard to the macroscopic physical property being modeled, without actual direct measurement thereof. An accurate value for the macroscopic physical property, such as oxygen permeation rate, can thereby be obtained in minutes, or less, instead of several weeks. The invention is of course also applicable to other macroscopic physical properties, although the savings of time and expense may not be as dramatic as in the case of permeation rate. Therefore, the rapid estimation of permeation rate, particularly oxygen permeation rate, is a principal utilization of the invention.

Figure 2:
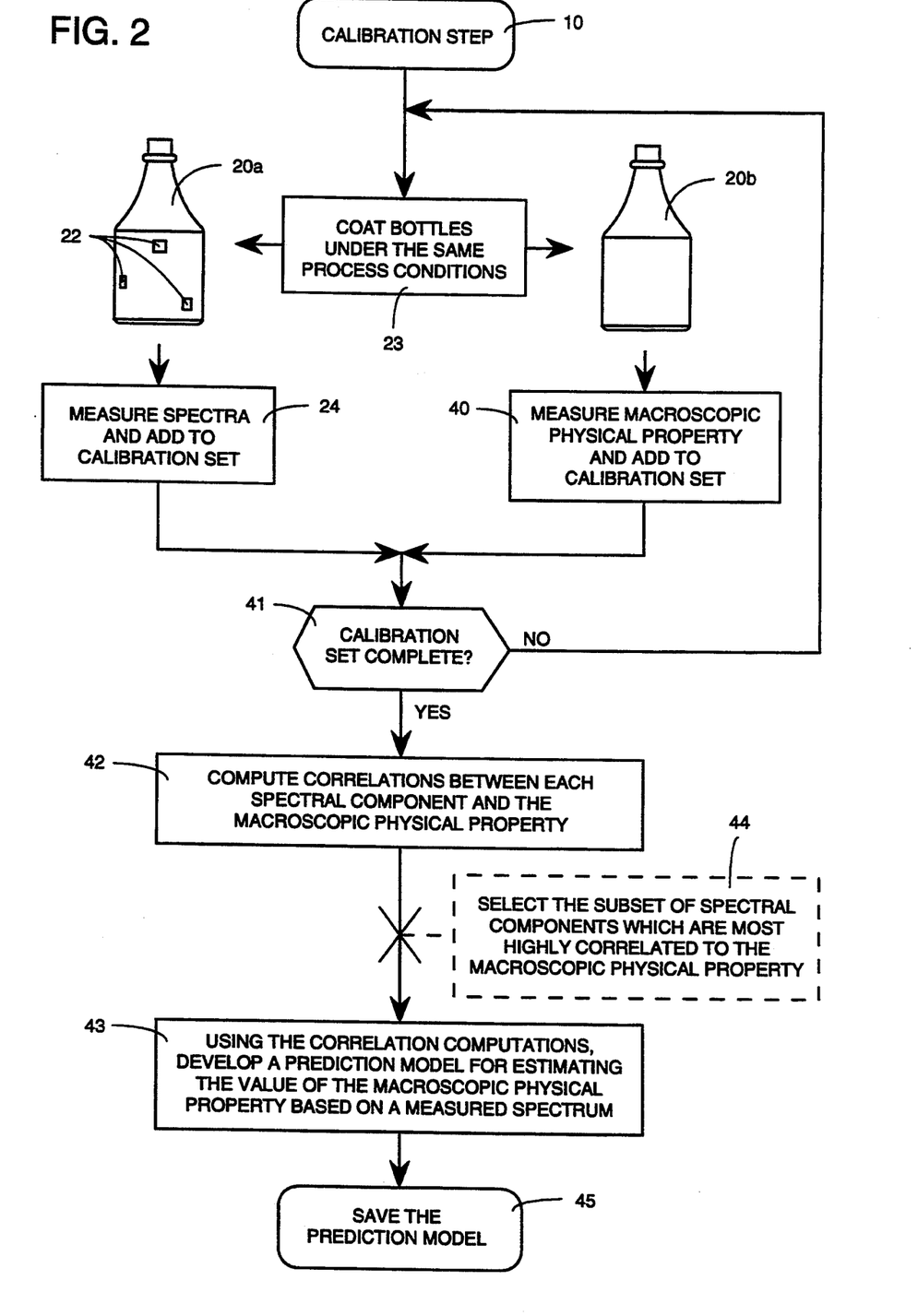
FIG. 2 is a detailed schematic diagram for the calibration step of the embodiment depicted in FIG. 1.

Referring to FIG. 2, the preparation of the prediction model 12 is illustrated with regard to a coating applied to plastic containers 20$a$ and 20$b$. Container 20$a$ is an "analysis" container, and carries a set of "witness" sample collectors 22 attached at various locations on the exterior surface of the container 20$a$. A set of four witness sample collectors 22 are preferably used, although only three are visible on the container 20$a$ as illustrated. The container 20$a$ is prepared for coating by first degreasing and drying in the normal manner. The witness sample collectors 22 are then attached to the container exterior using double sided tape. The locations selected for placement of the witness sample collectors 22 are not critical, but would correspond, for example, to areas of particular interest in the coating process. Each witness sample collector 22 is a silicon chip measuring 10 mm by 15 mm in area. The witness sample collectors 22 are preferably all diced from the same lot of wafers, for example, <100> oriented, P-doped silicon wafers of nominal resistivity 11–25 ohm-cm, 0.4 mm thick and polished on both sides. As discussed in greater detail below, these preparations may be deviated from within the scope of this invention, and in later described embodiments, the witness sample collectors 22 are eliminated altogether. In this embodiment, however, the witness sample collectors 22 are coated along with the container 20a, and serve as a convenient means for examining the coating applied thereto.

The other container 20b is considered to be a "control" container with respect to the macroscopic physical property of interest. Although it is understood that this invention is applicable to the determination of many different macroscopic physical properties, this embodiment will consider modeling of oxygen permeation rate as a principal example. After coating, the container 20b will be tested for its actual oxygen permeation rate, and therefore receives only the preparatory steps of degreasing and drying prior to the coating operation.

Figure 8:
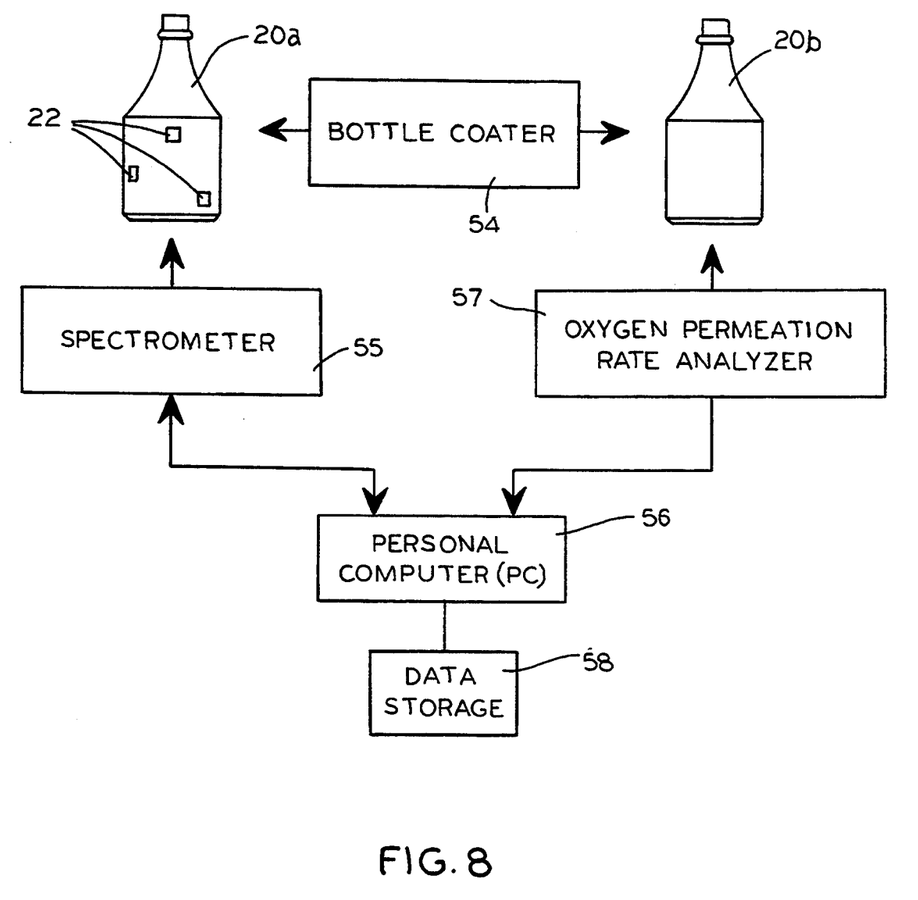
FIG. 8 is a block diagram of apparatus for preparing the prediction model.

A coating process represented by block 23 is performed on both containers 20a and 20b, by a battle coater 54 (FIG. 8). For the purpose of this embodiment, a barrier coating for reducing the oxygen permeation rate is considered. For example, the coating applied may be an exterior glassy film of nominal silicon dioxide ($SiO_2$), deposited by means of a low temperature plasma deposition reactor. The containers 20a and 20b are preferably coated in the same coating batch, e.g. with both containers 20a and 20b in the same treatment chamber at the same time. Alternatively, if same-batch processing is impracticable, then the containers 20a and 20b may be coated in different batches run under the same process conditions. Although same-batch processing is preferred, the short term repeatability of modern coating equipment is sufficient to ensure that both containers 20a and 20b will be coated nearly the same provided that the same process conditions are maintained from batch-to-batch.

Figures 3, 4, 5, 6, 7:
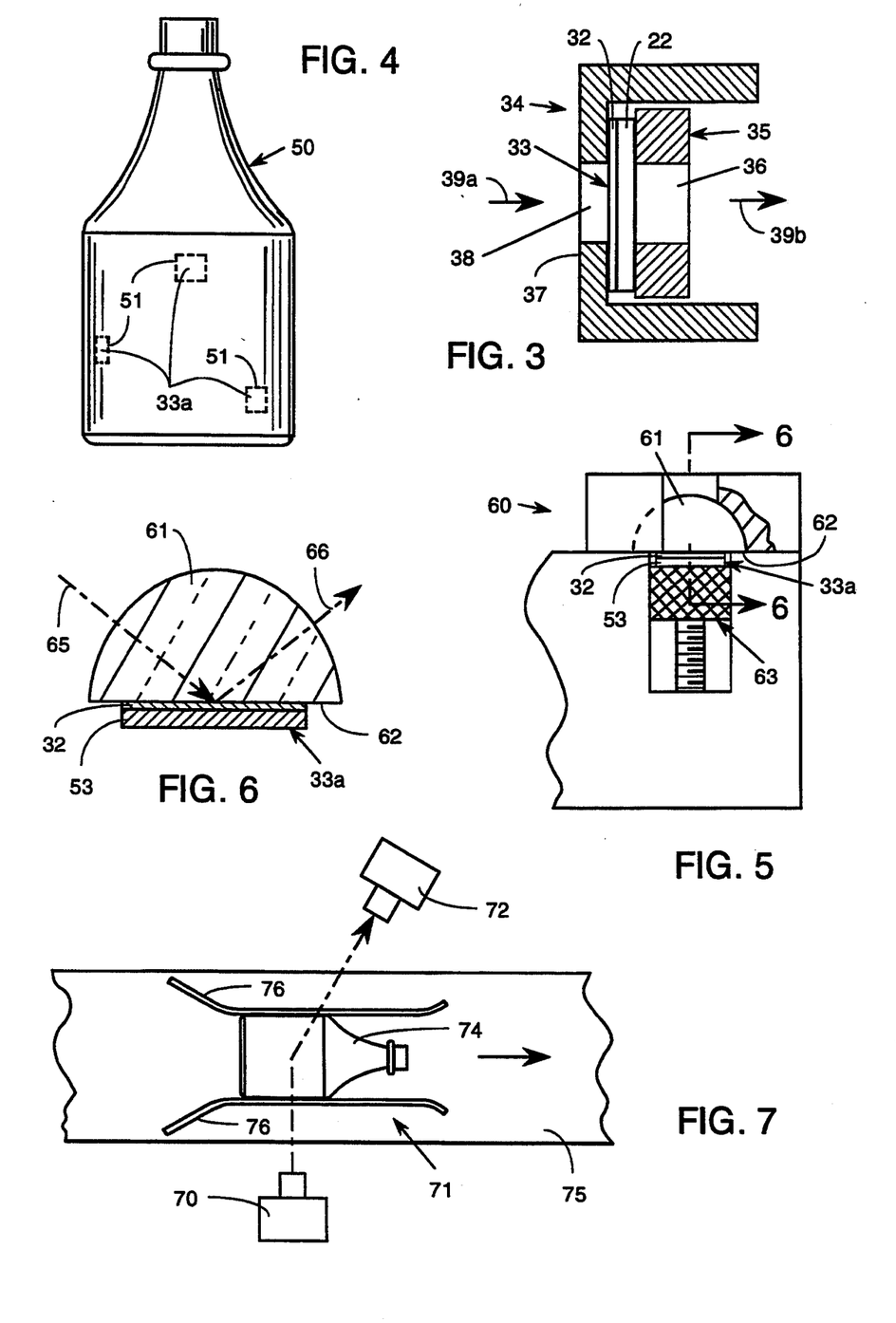
FIG. 3 is a side view of a witness sample which forms a part of the analysis container of FIG. 2, in which the witness sample is mounted in a spectroscopic test fixture which forms a part of the embodiment depicted in FIG. 1.
FIG. 4 is a plan view of an analysis container used in a second embodiment of the invention.
FIG. 5 is a side view of a witness sample which forms a part of the analysis container of FIG. 4, in which the witness sample is mounted in a spectroscopic test fixture which forms a part of the embodiment depicted in FIG. 4.
FIG. 6 is a sectional view taken on line 6—6 of FIG. 5.
FIG. 7 is a top plan view of a third alternate embodiment of the invention.

Referring to FIGS. 2 and 3, the coated container 20a is subjected to spectroscopic analysis as indicated in block 24 by a spectrometer 55 (FIG. 8). The spectroscopic analysis is preferably performed in the infrared ("IR") spectrum, although the invention in general is not limited thereto. To perform the spectroscopic analysis, the witness sample collectors 22, with a coating 32 now applied, are carefully peeled off from the container 20a so as not to crack the underlying witness sample collector 22. Hereinafter, the combination of the witness sample collector 22 with the coating 32 applied is collectively referred to as a "witness sample" 33. Once removed, each of the four witness samples 33 are, in turn, backside scrubbed to remove any residue from the tape used to hold the witness sample collector 22 on the container 20a, and then placed in a test fixture 34 (FIG. 3) adapted for holding the witness sample 33 during the IR spectroscopy. In particular, the test fixture 34 may form a part of a commercially available spectrometer, as described below, or may be a custom adapter jig therefor. The test fixture 34 illustrated in FIG. 3 is a conventional magnetic sample holder, in which a magnet 35 with a central window opening 36 holds witness sample 33 against an end wall 37 of the fixture 34. The end wall 37 is also provided with a central window opening 38. This arrangement permits normal-incidence transmission of IR radiation directly through the witness sample 33, as indicated by arrows 39a and 39b.

It should be noted that the illustrated thickness of the coating 32 in FIG. 3, and also in the other embodiments to follow, is highly exaggerated in scale with respect to the thickness of the witness sample collector 22. The coating 32 in actuality is extremely thin with respect to either the underlying witness sample collector 22 or the walls of the article coated, and would not be discernible if portrayed to scale. This is important to understand because the invention is most effective when practiced on the types of thin films which are currently in popular use in the art, for example, coatings with a thickness of roughly 300 nm (nanometers) or less. Of course, the invention is still completely usable with coatings thicker than 300 nm, but as the coating thickness increases, the spectroscopic analysis may degrade in sharpness, or precision, resulting in decreased accuracy of the prediction model 12.

One example of a suitable commercial spectrometer as used by applicant in performing the spectroscopy for this invention is a Fourier Transform IR (FTIR) spectrometer, model no. MB155, manufactured by Bomem. The spectrometer in this embodiment is operated in normal-incidence transmission mode, with the witness sample 33 positioned close to the detector in a "microfocus" position that illuminates a central (square millimeters), sample region of approximately 3 $mm^2$ (square millimeters). A raw sample spectrum for each of the four witness samples 33 is then obtained by performing 128 scans in the range from 430 $cm^{-1}$ (wavenumber) to 4010 $cm^{-1}$ with a resolution of 8 $cm^{-1}$. Each raw sample spectrum thus obtained is then corrected by unity subtraction of a reference spectrum to produce a corrected spectrum. The reference spectrum is obtained separately (not shown) using an uncoated silicon witness sample collector (also not shown) from the same wafer lot as the witness sample collectors 22 used on container 20a. This correction is performed to cancel out, at least partially, absorption characteristics due to the witness sample collector 22 itself, leaving principally the absorption due to the coating 32 alone in the corrected sample spectrum. Each corrected sample spectrum is then further corrected for baseline offset, resulting in a final sample spectrum. The foregoing process is performed for each of the four witness samples 33 on the analysis container 20a. A composite spectrum is then constructed by coherently averaging the final sample spectra from all four witness samples 33. The composite spectrum is thus a single spectrum which corresponds to the analysis container 20a in the aggregate.

The Bomem spectrometer described above operates under the control of conventional computer such as, for example, a personal computer (PC) 56 (FIG. 8) known to those skilled in the art as an IBM compatible PC. Accessories provided with the commercially available Bomem spectrometer include a parallel data interface to the PC, and software executable on the PC for carrying out the above described spectroscopy. The spectrometer PC software also includes facilities for storing the composite spectrum ultimately produced as a file on a disk drive on the PC, referred to herein as a composite spectrum file. The composite spectrum file containing the spectral data is thereby available to other software executing on the PC for further processing as described below.

Referring again to FIG. 2, after coating of the control container 20b is completed, an actual measurement of at least one macroscopic physical property of the control container 20b is performed, as indicated in block 40. For example, this embodiment considers the macroscopic physical property of oxygen permeation rate, and so that may be the property measured in block 40. Specifically, a commercially available oxygen permeation rate analyzer 57 (FIG. 8) may be utilized to directly measure the actual oxygen permeation rate of container 20b. One such analyzer which has been found by applicant to be suitable for this purpose is manufactured by Modern Controls, namely an Oxtran $O_2$ whole-package permeation analyzer (not shown). Due to the very slow rate and low levels of oxygen permeation, direct measurement of oxygen permeation rate in this manner typically requires a test run of several weeks, typically up to eight weeks. Measurement of the macroscopic physical property, or the actual oxygen permeation rate in this example, produces a numerical result, or value, representative of the quantity, or magnitude, of the property being measured.

Collectively, all of the spectra and quantitative measurements of the macroscopic physical properties corresponding thereto, are stored together in a data structure referred herein to as a calibration set. The calibration set is maintained as a data file on a disk drive, or other suitable storage media 58 (FIG. 8), within a computer which will process the calibration set as described in greater detail below. Preferably, the same PC as used for the spectroscopy described above may be used for this purpose, although the transfer of the various files between computer systems and the sharing of files over networks are also well known in the art and may be utilized with this invention. The calibration set may be structured as a list containing two associated entries for each sample run, those entries being (1) the numerical value corresponding to the macroscopic physical property measurement for the sample obtained in block 40, and (2) a file name, specifying the composite spectrum file which contains the corresponding spectrum for the same sample, as obtained in block 24. As previously noted, the composite spectrum file is stored directly on the PC as a part of the spectroscopy operation. The numerical value corresponding to the macroscopic physical property is typically a single number, and may be therefore be easily entered manually into the calibration set.

After completing both tests and recording the respective results at blocks 24 and 40, a decision is made at block 41 as to whether sufficient data has been collected for the current calibration step 10. The calibration step 10 has somewhat of a statistical nature, in that the quality, or accuracy, of the prediction model finally produced depends on (a) the number of samples included in the calibration set, and (b) the range of process conditions used in obtaining the samples in the calibration set. The first criteria (a) should be self-evident to those skilled in the art. If a greater number of samples are included in the calibration set, then the values obtained will tend to be distributed about statistical norms, and therefore be more insensitive to individual aberrations. The second criteria (b) is important in ensuring that the prediction model 12 developed is valid over a range of process conditions. Specifically, the prediction model 12 should preferably be valid over that range of process conditions for which the prediction model 12 is expected to be used. In other words, while it would be possible to construct a calibration set which includes samples taken using only one process condition, the resulting prediction model 12 could be expected to yield accurate results only for that single process condition, or process conditions nearly the same. According to the invention, however, it has been discovered that by including samples in the calibration set which are obtained over a range of process conditions, a prediction model 12 can be achieved which is usable and valid over an entire range of process condition. For example, the prediction model 12 may be desired to be used in a production environment which is expected to produce various coated containers in which the coatings range in thickness from approximately 16 nm to 300 nm. In that case, the calibration set would preferably include samples prepared with various thicknesses distributed throughout that range. Process conditions other than thickness may also be varied over specific ranges, including temperature, pressure, and chemical constituents used in the coating process.

A more detailed discussion of the range of values for which the prediction model 12 is valid is presented below in relation to the actual computations used for producing the prediction model 12. For now, it is sufficient to note that the samples included in the calibration set should be sufficient in number and should cover a predetermined range of process conditions. As a general guideline, applicant has found that a calibration set which includes 15 samples distributed approximately evenly over a range of thicknesses of 16 nm to 300 nm has been found to yield a prediction model with satisfactory accuracy over the same range of process conditions. Therefore, the choice of the number of samples and the process conditions under which the samples are obtained, may vary, and is decided upon based the prediction model 12 desired. The test at block 41 of FIG. 2, therefore, is a decision as to whether the samples for the calibration step 10 have been completed. If more samples are needed, then a branch is taken back to block 23, where additional samples are taken, possibly under different process conditions as discussed above. A loop is thereby established to obtain samples until the calibration set is complete. Once the calibration set is found to contain all of the desired samples at block 41, a branch is taken on to block 42.

Still referring to FIG. 2, correlation computations are performed in block 42 to produce the correlation coefficients for each spectral component with respect to the macroscopic physical property of interest. The computation of correlations in general is known to those skilled in the art, and has been previously used as a means for performing chemical assays of an unknown material. For example, it was known in the prior art that certain atomic elements and bonds therebetween exhibit characteristic absorption and/or reflection with regard to electromagnetic radiation. correlations between the absorption-reflection patterns and the underlying atomic components and sub-structures have thus been used for component analysis. Due to the extremely complicated nature of the atomic bonding mechanisms involved in thin films, the prior art has been unable to accurately and quantitatively associate atomic effects with macroscopic physical properties. Specifically, the mere knowledge that a certain component or atomic bond exists in a thin film sample has not previously allowed those skilled in the art to accurately predict, or provide an estimated numerical value for, the macroscopic physical properties of that sample.

Applicant has now made an important discovery in this field which can be summarized as follows. According to the prior art knowledge, as described above, spectroscopic analysis can be correlated to atomic properties of the material under investigation. However, the atomic processes which control the macroscopic behavior, or physical characteristics of a material are in some cases known to certain extent, but in other cases are completely unknown. According to the present invention, it is now possible to in essence "bypass" an understanding of mechanisms by which atomic structure effects macroscopic physical properties, and instead directly correlate spectroscopic analysis with a macroscopic physical property of interest. It would not be necessarily apparent that such correlations could be formed at all. Indeed, it will be found that not all physical properties can be modeled in this way. In order for the teaching of this invention to be effective, it is necessary that a causal nexus exist between an underlying atomic structure and the macroscopic physical property of interest. Note again that it is only necessary for such a causal nexus to exist, not to be able to understand or quantify it. For example, applicant has verified through direct experimentation that the invention is extremely useful in modeling oxygen permeation rate, which is an otherwise extremely difficult property to measure. Conversely, if the invention is applied for modeling the refractive index of materials in visible light based on IR spectroscopy, then the resulting correlations may be poor and the results unusable. Therefore, the invention is applicable to those situations in which both (a) a spectrum for a material correlates to an atomic structure in the material, and (b) the atomic structure directly affects a macroscopic physical property of the material, e.g. that the atomic structure "correlates" well to the macroscopic physical property of interest. It is important to note in the foregoing that neither an exact identification of the atomic structure nor knowledge of the effects that the atomic structure has on the macroscopic physical property are necessary; it is only necessary for the respective correlations to exist. And although it may seem as though there are two separate correlations involved; one between the spectrum and the atomic structure, and a second correlation between that atomic structure and a macroscopic physical property, another important teaching of the invention is that if both of these correlations exist, then it is possible to derive a single correlation directly from spectrum to macroscopic physical property. Furthermore, it is not necessary according to the invention to separately verify the existence of the separate correlations just described. Instead, the direct correlation from spectrum to macroscopic physical property is determined experimentally, and if sufficiently strong correlations are found, then a prediction model 12 according to the invention is usable, and no further analysis is necessary.

The specific correlation computations performed in block 42 may be performed, for example, using generalized commercially available software. In particular, the software package sold under the trademark PLSplus, version 2.1, marketed by Galactic Industries Corporation, Salem, NH, has been found to be suitable. The PLSplus package is usable in either LabCalc or GRAMS/386, both of which are also available from the aforementioned Galactic Industries Corporation. The LabCalc environment executes directly under a Disk Operating System (DOS) on an IBM compatible PC. The GRAMS/386 environment, on the other hand, executes under the the well known WINDOWS environment, the latter being a graphical environment separately available from Microsoft, Inc., and also executable on an IBM compatible computer using an Intel 80386 microprocessor. The GRAMS/386 environment has been found by applicant to provide substantially faster execution times, and is therefore generally preferred. In this embodiment, the PLSplus software is preferably executed on the same PC as used in performing the spectroscopy described above.

The PLSplus software includes conventional routines to compute raw correlations between each spectral component in a given spectrum and the macroscopic physical property of interest. The raw correlations for individual spectral components may be positive or negative, and may be strong or weak. Assuming that the correlation coefficients are standardized between $+1$ (strongest positive correlation) and $-1$ (strongest negative correlation), then the correlations are considered "strong" when the coefficients are near $+1$ or $-1$. Conversely, coefficients near zero indicate weak correlations. If a particular correlation includes at least some strongly correlated spectral components, then the accuracy of the prediction model 12 should be quite good. If on the other hand, none of the spectral components correlate strongly to the macroscopic physical property of interest, then the accuracy of the prediction model 12 for the particular macroscopic physical property under investigation will be poor and may or may not be usable, depending upon the accuracy desired.

The subsequent processing steps assume that at least some spectral components strongly correlate to the macroscopic physical property of interest. In that case, a prediction model 12 can be computed as shown in block 43. However, before proceeding to block 43, an optional step shown by dotted lines 44 may be performed in order to improve the accuracy of the prediction model 12 eventually produced. Specifically, the optional step 44 may be used to select a subset of the spectral components for further processing, in which the selected subset contains only those spectral components that are the most strongly correlated to the particular macroscopic physical property of interest. For example, a spectral subset may include only those components, or "bands" of adjacent spectral components, which have correlation coefficients with an absolute value greater than a predetermined threshold value. The optional step 44 is not essential to the invention, since a prediction model 12 may be produced based simply on the entire spectrum. However, the step 44 is generally preferred because it results in a more accurate model, particularly in those cases where a relatively fewer number of spectral components are strongly correlated. The PLSplus software includes a facility for specifying specific spectral components or bands to be used in subsequent computations, which may be used to perform the operation indicated in block 44, if desired.

In block 43, the desired spectral components (whole spectrum or selected subset) are further processed using a multivariate regression analysis to produce a prediction model. As generally known to those skilled in the art, multivariate regression analysis may be performed by the known techniques of partial least squares, principal components regression, and others. In this embodiment, the aforementioned PLSplus software also provides a capability to perform the multivariate regression analysis. Specifically, the PLSplus software includes a routine referred to as a "PLS-1" algorithm which performs a multivariate regression analysis referred to as a Prediction Residual Error Sum of Squares (PRESS) calculation. The PRESS calculation first computes a number of different prospective modeling functions with an increasing order of complexity, or "factor" number, as generally known to those skilled in the art. Each prospective modeling function is a function of "n"

variables, where "n" is the number of spectral components selected for inclusion in the PRESS calculation. By default, prospective modeling functions are computed for a number of factors equal to half of the number of samples in the calibration set. For example, if the calibration set includes 14 samples, then seven prospective modeling functions are computed by default, corresponding to factors one through seven, respectively. The default choice for the number of prospective modeling functions may of course be overridden, if desired, to specify a greater or lesser number of prospective modeling functions to be computed. Once the prospective modeling functions have been calculated, the PRESS routine also performs a cross-validation in the known manner to compute the expected prediction error corresponding to each prospective modeling function using a one-sample-out cross-validation rotation. The estimated error typically drops rapidly with an increasing number of factors until a minimum is reached. The prospective modeling function which exhibits the minimum estimated prediction error is then preferably chosen to be the prediction model 12.

Finally, at block 45 the prediction model 12 is saved on disk, or other suitable storage media. The prediction model 12 as produced by the PLSplus software used in this embodiment is a formatted file, encoded with information including (a) the order, or "factor" number of the modeling function, (b) the number of spectral components used, "n", and the specific spectral components, or bands, which participate in the modeling equation, and (c) the coefficients for the modeling equation.

Referring again to FIG. 1, the prediction model 12 developed by the calibration step 10 described above can now be utilized to estimate a macroscopic physical property of a coating in the production step 11. Typically, this aspect of the invention would be used, for example, to verify that a coating as applied has the desired physical characteristics as a part of a quality control program or for product statistics. The production step 11 begins at block 13, where a number of containers 14$a$ and 14$b$ are coated using similar process conditions. Container 14$a$ is an analysis container, intermingled with the production containers 14$b$ during the coating process in a manner determined by the information desired for quality control or statistical purposes. For example, it may be desired to include one analysis container 14$a$ in each coating batch of production containers 14$b$, or one analysis container 14$a$ for each 100 or 1,000 production containers 14$b$ (not necessarily in the same batch), and so on. These would of course be the same quality control or statistical procedures as used in the prior art, except that according to the invention, the analysis container 14$a$ is analyzed by spectroscopic analysis rather than direct measurement of the macroscopic physical property of interest. In that regard, the analysis container 14$a$ in this embodiment receives one or more witness sample collectors 22 prior to coating in the same manner as described above in relation to the calibration step 10. The analysis container 14$a$ is then coated as shown in block 13 along with the remainder of the production containers 14$b$. The production containers 14$b$ then represent the finished product for the coating process, as represented by arrow 15.

After coating, the witness sample collectors 22 are removed from the analysis container 14$a$ and subjected to spectroscopic analysis as indicated in block 16, again in a manner similar to that used in the calibration step 10 described above. However, in the production step 11 the resulting spectrum obtained in block 16 is used as input data for the prediction model 12. It would be understood by those skilled in the art that evaluation of the prediction model 12 is carried out by a suitable computer with appropriate software. For example, the aforementioned PLSplus software, running on an IBM compatible PC, includes routines suitable for evaluating the prediction model 12 based on the measured spectrum 16.

The result of evaluating the prediction model 12 for the particular spectrum from block 16 results in an estimated value for the macroscopic physical property of interest, as represented by block 17. Again considering the example of determining oxygen permeation rate, the numerical result at block 17 would be in effect an accurate indication of that property. In fact, the computation of oxygen permeation rate is a principal application of the invention, since it results in an amazing reduction in both the time and the complexity of the apparatus required when compared to prior methods for direct measurement of the same property (minutes versus weeks, respectively).

Finally, the estimated macroscopic physical property from block 17 is output at block 18, e.g. utilized for an appropriate purpose such as the aforementioned quality control or product statistics. Even though the estimated value 17 is not necessarily as exact as that which could be obtained by direct measurement, it has nevertheless been found by applicant to be a highly accurate estimation thereof. With suitable care with respect to preparation and verification of the prediction model 12$b$ as described herein, an estimation with a Standard Error of Prediction (SEP) of less than 10% relative should be easily attainable. And for applications such as quality control and product statistics, where a general indication rather than absolute accuracy is desired, this invention provides a drastic improvement in both speed and simplicity.

As an optional step (not shown) it may be desirous to separately verify the prediction model 12 based upon containers from the finished product batch 14$b$. In the calibration step 10, the results may be subject to self-prediction, e.g. the result has been optimized with respect to the samples only in the calibration set. The true accuracy of the prediction model 12 may be verified independently by performing actual, direct measurement of the macroscopic physical property of interest for some of the finished product containers 14$b$, and comparing the value thus obtained to the value 17 estimated by the prediction model 12. In tests of this type performed by applicant, the prediction model 12 has been found to have an accuracy acceptable for production purposes, i.e. for quality control or product statistics. However, if a particular verification of this type should result in an unacceptable accuracy, then it would be necessary to repeat the calibration step 10, as necessary, until a suitable prediction model 12 is obtained. For example, the calibration step 10 could be performed with a different set of process conditions, perhaps with a more narrow range of process conditions, or with more samples, and so on. Of course, once the prediction model 12 has been verified in this way, further direct measurements would again be unnecessary.

As one additional comment on the first embodiment described above, it was previously noted that the best results are obtained when all of the witness sample collectors 22 are diced from the same wafer lot. If this is not practicable, the effect of poorly matched witness sample collectors 22 is manifest as a "noise" factor introduced into the correlation computations. In particular, the "reference" spectrum mentioned above may not be accurate with respect to witness sample collectors 22 from another wafer lot. It has been found in practice that even when collectors 22 from different lots are used, the resulting prediction model 12 is still acceptably accurate, albeit not as good as when all collectors 22 are from the same lot. Therefore, for the best accuracy, control should be exercised over the witness sample collectors 22 to maintain consistent "reference" characteristics. For example, different wafer lots could be selected on a basis of matching to some degree with respect to the respective "reference" spectra.

Referring to FIGS. 4–6, a second embodiment employs IR spectroscopy in an attenuated total reflection (ATR), or "internal reflection" mode in carrying out the invention. With ATR spectroscopy, the bulk structure underlying the coating 32 does not participate in the spectroscopy, and therefore the witness sample collectors 22 used in the previous embodiment are not needed. Instead, witness samples 33a are obtained by cutting out small sections of a coated container 50, as shown by the dotted line areas 51 in FIG. 4. Thus, container 50 of this embodiment serves the same purpose as the analysis container 22a of the previous embodiment, except that no special preparations are needed for the container 50. The witness samples 33a may be cut out, for example, at the same corresponding locations used for the witness sample collectors 22 on container 22a in the preceding embodiment. In this embodiment, however, the witness samples 33a include the material of the container 50 itself as a substrate 53, with the coating 32 applied thereon.

Referring particularly to FIGS. 5 and 6, each witness sample 33a is placed in an ATR test fixture 60 for spectroscopic analysis. The test fixture 60 may include a hemispherical internal reflection element 61 with a flat bottom surface 62. A clamp mechanism 63 presses the witness sample 33a against the internal reflection element 61, with the coating 32 facing the bottom surface 62. Incident radiation represented by broken line arrow 65 thus passes through the internal reflection element 61, is partially absorbed by the coating 32, and exits the internal reflection element 61 as shown by broken line arrow 66. The Bomem spectrometer previously mentioned includes optical apparatus and software for performing the ATR spectroscopy, and so is also usable with this embodiment. An ATR fixture 60 suitable for quantitative ATR spectroscopy, and adapted to operate in the Bomem spectrometer, is the model SEA-BO3 reflection attachment manufactured by Harrick Scientific.

The second embodiment utilizes the same calibration step 10 and production step 11 as in the preceding embodiment. The only difference is the manner in which the spectroscopic analysis is performed, illustrating the flexibility of application of the invention. Applicant has determined that the overall results obtainable using this embodiment are generally comparable to the results attainable using the first embodiment described above. Further, the second embodiment does not require witness sample collectors 22, and so is somewhat easier to perform and does not require the aforementioned concern over matching of witness sample collectors 22. Therefore, the second embodiment is generally preferred over the first embodiment.

Referring now to FIG. 7, a third embodiment of the invention employs IR spectroscopy in an external reflectance mode, e.g. simple reflection off of the coating 32, without using an internal reflection element 61. Again, the principle and operation of this embodiment is similar to the first embodiment described above, in that the same calibration step 10 and production step 11 are used with yet another type of spectroscopy. In this embodiment, an illuminating source 70 of a reflectance spectrometer apparatus (not shown in full) is disposed above and to one side of a test station 71. A spectrometer detector 72 is arranged above the test station 71 across from the source 70, so as to receive radiation from the source 70 which is reflected externally off of a surface (e.g. the coating, not separately shown) of a test container 74 positioned in the test station 71. The source 70 and detector 72 are supported by suitable linkages as known in the spectroscopy arts, and may be provided with an adjustment for the angles of incidence and reflection with respect to the container surface.

An automated conveyance such as, for example, a moving belt 75 may be utilized to automatically deliver the container 74 to the test station 71. Alternatively, many other known conveyances may be utilized, including either manual or robotic positioning. Preferably, the test station 71 includes a positioning jig such as, for example, guide rails 76 as illustrated. Again, any other known positioning expedient may be utilized to accurately register the container 74 with respect to the spectrometer source 70 and detector 72 for testing, including mechanical stops and position sensors (both not shown).

In the FIG. 7 embodiment, incident radiation reflects directly from the surface coating to be tested. In that case, the spectrometry is preferably performed on a portion of the container 74 which is as flat as possible to allow precise alignment of the source 70 and detector 72. Alignment of the spectrometry components is thus more complicated in this embodiment and may employ, for example, position sensors, including machine vision systems, to achieve the needed alignment. Still, even with auxiliary aids to alignment, the spectroscopy obtained is likely to be less accurate than in the preceding embodiments where a precision fixture was used. Nevertheless, this third embodiment is highly adaptable to automated testing, and may therefore be used where it is desired to rapidly test a large number of samples in an automated manner, albeit with some potential decrease in accuracy.

It will be understood by those in the art that the present invention may be modified in a number of aspects without departing from the spirit of the invention. For example, spectroscopy utilizing other than IR radiation is well known and usable with this invention. Further, the invention can be applied for the measurement of interior coatings, particularly in the second embodiment, by simply reversing the witness sample 33a to perform spectroscopy on the coated side thereof.

I claim:

1. A method for measuring the oxygen permeation rate of an unknown solid, inorganic thin film coating applied on a surface of a plastic container for a consumable food product, said solid thin film coating having a thickness ranging from approximately 16 nanometers to 300 nanometers, the method comprising the steps of:

(a) preparing a prediction model which accepts as an input at least one input spectral component value corresponding to absorption of electromagnetic radiation in at least one frequency band of the radiation, and which outputs an estimated measurement for oxygen permeation rate based on said input;

(b) performing spectroscopic analysis of the unknown thin film coating on said plastic container to obtain at least one sample spectral component value corresponding to the absorption of electromagnetic radiation in said at least one frequency band by the unknown thin film coating; and (c) evaluating the prediction model with said at least one sample spectral component value as the input spectral component value, wherein the output of prediction model is thereby a measurement of the oxygen permeation rate exhibited by the unknown thin film coating on said plastic container.

2. The method of claim 1, in which step (a) for preparing the prediction model comprises the steps of:

(d) applying a thin film analysis coating having a thickness ranging from approximately 16 nanometers to 300 nanometers to an analysis container under a first set of coating process conditions;

(e) applying a thin film control coating having a thickness ranging from approximately 16 nanometers to 300 nanometers to a control container under approximately the same process conditions as said first set of coating process conditions;

(f) performing spectroscopic analysis of the analysis coating to obtain at least one analysis spectral component value corresponding to the absorption of electromagnetic radiation in said at least one frequency band by the analysis coating;

(g) measuring the oxygen permeation rate exhibited by the control container to thereby obtain a measured value for the oxygen permeation rate;

(h) computing correlations between each of said at least one analysis coating spectral component values and the measured value for the oxygen permeation rate; and (i) performing multivariate regression analysis on the correlations with respect to the measured value for the oxygen permeation rate to produce the prediction model as an equation which maps spectral components as inputs to an estimated value for the oxygen permeation rate as an output.

3. The method of claim 2 in which: the spectroscopic analysis of the analysis coating in step (f) produces a plurality of analysis coating spectral component values;

correlations are computed in step (h) for each of said plurality of analysis coating spectral component values;

a subset of spectral components is selected to include only those spectral components which are most highly correlated to the oxygen permeation rate according to the correlations computed in step (h); and the multivariate regression analysis in step (i) is performed on the basis of said subset of spectral components.

4. The method of claim 2 in which the spectroscopic analysis in steps (b) and (f) for the unknown thin film coating and the analysis coating, respectively, is performed in a normal incidence transmission mode, and comprises the steps of:

(j) affixing a witness sample collector onto the respective plastic containers prior to application of the thin film coating;

(k) removing the witness sample collector after application of the respective thin film coating;

(l) analyzing the thin film coating applied to the witness sample collector in a normal incidence transmission mode spectrometer to obtain at least one raw spectral component value; and (m) correcting said at least one raw spectral component value by unity subtraction of spectral components corresponding to the absorption characteristics of the witness sample collector to produce said at least one spectral component value.

5. The method of claim 2 in which the spectroscopic analysis in steps (b) and (f) for the unknown thin film coating and the analysis coating, respectively, is performed in an attenuated total reflection mode, and comprises the steps of:

(j) removing a portion of the respective plastic container which includes the thin film coating; and (k) analyzing the thin film coating on the removed portion of the respective plastic container in an attenuated total reflection mode spectrometer.

6. The method of claim 2 in which the unknown thin film coating is applied on an external surface of the plastic container, and the spectroscopic analysis in step (b) for the unknown coating is performed in an external reflection mode, and comprises the steps of:

(j) placing the container in a test station; and (k) analyzing the unknown thin film coating with the container in the test station using an external reflection mode spectrometer.

7. The method of claim 6 in which the measurement of the unknown thin film coating in steps (b) and (c) is repeated for a plurality of said containers by sequentially placing each of said containers in the test station.

8. The method of claim 7 in which the sequential placing of each of said containers in the test station is accomplished by automatic means.

9. An apparatus for measuring the oxygen permeation rate of an unknown solid, inorganic thin film coating applied on a surface of a plastic container for a consumable food product, said solid thin film coating having a thickness ranging from approximately 16 nanometers to 300 nanometers, comprising:

means for preparing a prediction model which accepts as an input at least one input spectral component value corresponding to absorption of electromagnetic radiation in at least one frequency band of the radiation, and which outputs an estimated measurement for oxygen permeation rate based on said input;

means for performing spectroscopic analysis of the unknown thin film coating on said plastic, container to obtain at least one sample spectral component value corresponding to the absorption of electromagnetic radiation in said at least one frequency band by the unknown thin film coating; and means for evaluating the prediction model with said at least one sample spectral component value as the input spectral component value, wherein the output of prediction model is thereby a measurement of the oxygen permeation rate exhibited by the unknown thin film coating on the plastic container.

10. The apparatus of claim 9, wherein the means for preparing the prediction model comprises:

means for applying a thin film analysis coating having a thickness ranging from approximately 16 nanometers to 300 nanometers to an analysis container under a first set of coating process conditions;

means for applying a thin film control coating having a thickness ranging from approximately 16 nanometers to 300 nanometers to a control container under approximately the same process conditions as said first set of coating process conditions;

means for performing spectroscopic analysis of the analysis coating to obtain at least one analysis coating spectral component value corresponding to the absorption of electromagnetic radiation in said at least one frequency band by the analysis coating;

means for measuring the oxygen permeation rate exhibited by the control container to thereby obtain a measured value for the oxygen permeation rate;

means for computing correlations between each of said at least one analysis coating spectral component values and the measured-value for the oxygen permeation rate; and means for performing multivariate regression analysis on the correlations with respect to the measured value for the oxygen permeation rate to produce the prediction model as an equation which maps spectral components as inputs to an estimated value for the oxygen permeation rate as an output.

11. The apparatus of claim 10 in which the means for performing spectroscopic analysis for the unknown thin film coating and the analysis coating, respectively, each includes a witness sample collector, in which the witness sample collector is affixed onto the respective plastic containers prior to application of the thin film coating, and in which the apparatus further comprises:

means for analyzing the thin film coating applied to the witness sample collector in a normal incidence transmission mode spectrometer to obtain at least one raw spectral component value; and means for correcting said at least one raw spectral component value by unity subtraction of spectral components corresponding to the absorption characteristics of the witness sample collector to produce said at least one spectral component value.

* * * * *